| United States Patent [19] | [11] Patent Number: 4,515,736 |
|---|---|
| Deamer | [45] Date of Patent: May 7, 1985 |

[54] METHOD FOR ENCAPSULATING MATERIALS INTO LIPOSOMES

[75] Inventor: David W. Deamer, Woodland, Calif.

[73] Assignee: The Regents of the University of California, Berkeley, Calif.

[21] Appl. No.: 493,952

[22] Filed: May 12, 1983

[51] Int. Cl.$^3$ .......................... A61K 9/52; B01J 13/02
[52] U.S. Cl. ..................................... 264/4.3; 252/700; 264/4.6; 424/1.1; 424/9; 424/38; 424/88; 428/402.2; 436/829
[58] Field of Search ................................. 264/4.3, 4.6; 428/402.2; 436/829; 424/38

[56] References Cited

U.S. PATENT DOCUMENTS

| 4,016,100 | 5/1977 | Suzuki et al. | 264/4.3 |
| 4,229,360 | 10/1980 | Schneider et al. | 264/4.6 |
| 4,235,871 | 11/1980 | Papahadjopoulos et al. | 424/19 |
| 4,396,630 | 8/1983 | Riedl et al. | 424/199 X |

OTHER PUBLICATIONS

Z. T. Chowhan, et al., *Biochim. Biophys. Acta*, 266, (1972), 320–342, "Transport Through Lecithin Spherules".
Reeves et al., *J. Membrane Biol.*, 3, (1970), 123–141, "Water Permeability of Phospholipid Vesicles".
Papahadjopoulos et al., *Biochim. Biophys. Acta*, 135, (1967), 639–652, "Permeability of Phospholipid Model Membranes".
Reeves et al., *J. Cell. Physiol.*, 73, (1969), 49–60, "Thin-Walled Phospholipid Vesicles".
Szoka et al., *Ann. Rev. Biophys. Bioeng.*, 9, (1980), 467–508, "Comparative Properties and Methods of Preparation of Lipid Vesicles (Liposomes)".
Robinson, *Farady Society, Trans.*, #56, (1960), 1260–1254, "Light Scattering of Lecithin".
Zumbuchl et al., *Biochimica et Biophysics Acta*, 640, pp. 252–262, "Liposomes of Controllable Size in the Range of 40 70 180 nm by Definded Dialysis of Lipid/Detergent Mixed Micelles".
Deamer et al., *J. Mol. Evol.*, 18, (1982), 203–206, "Encap. of Macromolecules by Lipid Vesicles under Simulated Prebiotic Conditions".
Pick, *Arch. Biochem. Biophys.*, 212, 186–194, (1981), "Liposomes with Large Trapping Capacity Prepared by Freezing and Thawing . . . ".
Huang, *Biochemistry*, 8, pp. 344–351, (1969), "Studies on Phosphatidylcholine Vesicles".
Szoka et al., *Proc. Nat'l. Acad. Sci. U.S.A.*, 75, (1978), "New Procedure for Preparation of Liposomes . . . (REV)".
Mimms, *Biochemistry*, 20, pp. 833–839, (1981), "Phospholipid Vesicle Formation and Transmembrane Protein Incorporation . . . ".
Enoch, *Proc. Natl. Acad. Sci. U.S.A.*, 76, pp. 145–149, (1979), "Formation Properties of 1000-A-Diameter, Single-Bilayer Phospholipid Vesicles".

*Primary Examiner*—Richard D. Lovering
*Attorney, Agent, or Firm*—Majestic, Gallagher, Parsons & Siebert

[57] ABSTRACT

A novel encapsulation method is provided in which liposome dispersions are dried in the presence of a material to be encapsulated. As drying occurs, the individual liposomes fuse to form multilamellar structures which capture the material between lipid lamellae. Upon rehydration, lipid vesicles form which efficiently encapsulate the material.

13 Claims, No Drawings

METHOD FOR ENCAPSULATING MATERIALS INTO LIPOSOMES

FIELD OF THE INVENTION

The present invention relates generally to liposomes, and more particularly to a method for encapsulating materials, such as drugs, nucleic acids, proteins, reporter molecules, enzymes and the like, into liposomes. Liposomes formed in accordance with the present invention are useful in applications such as in vivo drug delivery and as diagnostic agents.

BACKGROUND OF THE INVENTION

Liposomes are unilamellar or multilamellar lipid vesicles which enclose a three-dimensional space. The membranes of liposomes are formed by a bimolecular layer of one or more lipid components having polar heads and non-polar tails. In an aqueous (or polar) solution, the polar heads of one layer orient outwardly to extend into the aqueous, or polar, solution and to form a continuous, outer surface. Unilamellar liposomes have one such bimolecular layer, whereas multilamellar vesicles generally have a plurality of substantially concentric bimolecular layers arranged rather like an onion.

Liposomes are well recognized as useful for encapsulating therapeutic agents, such as cytotoxic drugs or other macromolecules capable of modifying cell behavior, and carrying these agents to in vivo sites. For example, U.S. Pat. No. 3,993,754, inventors Rahman et al., issued Nov. 23, 1976, discloses an improved method for chemotherapy of malignant tumors in which an antitumor drug is encapsulated within liposomes and the liposomes are injected into an animal or man. U.S. Pat. No. 4,263,428, inventors Apple, et al., issued Apr. 21, 1981, discloses an antitumor drug which may be more effectively delivered to selective cell sites in a mammalian organism by incorporating the drug within uniformly sized liposomes. Drug administration via liposomes can have reduced toxicity, altered tissue distribution, increased drug effectiveness, and an improved therapeutic index.

Liposomes have also been used in vitro as valuable tools to introduce various chemicals, biochemicals, genetic material and the like into viable cells, and as diagnostic agents.

A variety of methods for preparing liposomes are known, many of which have been described by Szoka and Papahadjopoulos, *Ann. Rev. Biophysics Bioeng.* 9: 467–508 (1980). Also, several liposome encapsulation methods are disclosed in the patent literature.

For example, U.S. Pat. No. 4,235,871, inventors Papahadjopoulos and Szoka, issued Nov. 25, 1980, describes a method whereby large unilamellar vesicles can be formed which encapsulate large macromolecules. A principle disadvantage of this method is the exposure of the material to be encapsulated to organic solvent, such as diethyl ether, which may result in denaturation of sensitive proteins.

U.S. Pat. No. 4,016,100, inventors Suzuki et al., issued Apr. 5, 1977, describes the entrapment of certain pharmaceuticals in lipid vesicles by freezing the aqueous phospholipid dispersion of pharmaceutical and lipid. It is not clear as to the bio-availability of the total material encapsulated, and the technique may not be efficient for pharmaceuticals of a relatively polar nature. Also, the necessity for freezing, thawing and then separating large volumes is expensive for large-scale, commercial preparation.

Although encapsulation of therapeutic agents and biologically active compounds in liposomes has significant potential for delivering such materials to targeted sites in the human body and for diagnostic applications, producing encapsulated materials on a commercially feasible scale has been a problem. The current methods involve organic solvents or detergents which are expensive, difficult to remove, or present health hazards, and which may interact unfavorably with the therapeutic agents or biologically active molecules to be encapsulated.

It is an object of the present invention that a method be provided which is suitable for the encapsulation of a wide variety of materials, including biologically active macromolecules such as nucleic acids, polypeptides, and enzymes, and which has trapping efficiencies up to about fifty percent of the original material utilized for encapsulation.

It is a further object of the present invention to provide a method which is simple, avoids the use of organic solvents or detergents, and which is feasible and inexpensive for large-scale, commercial production of liposomes having materials encapsulated therein.

SUMMARY OF THE INVENTION

A method for encapsulating materials into liposomes comprises providing a first polar solution. The first polar solution has initial liposomes and a quantity of material to be encapsulated dispersed therein. Substantially all of the first polar solution is removed and a concentrated admixture of the initial liposomes and the quantity of material to be encapsulated is formed. The resultant liposomes are then readily recovered by hydrating the concentrated admixture. The resultant liposomes encapsulate from about 1 weight percent to about 50 weight percent (or greater) of the material. This value can be controlled by the original weight ratio of lipid to solute, and often reaches a maximum at approximately 10:1 lipid:solute ratios.

A preferred embodiment is wherein the first polar solution is aqueous. Use of water as a single, aqueous phase in which both the initial liposomes and the material to be encapsulated are dispersed avoids possible unfavorable interactions with the selected material for encapsulation and obviates the removal of organic solvents or detergents of prior methods. Instead, the water of the preferred embodiment can be readily removed with conventional equipment while forming the concentrated admixture of initial liposomes and material to be encapsulated. The inventive method can be conveniently practiced in commercial quantities, such as for pharmaceutical or diagnostic preparations.

A mechanism for the inventive encapsulation process is believed to be that the initial liposomes are unable to maintain a stable bilayer structure during removal of the first polar, or aqueous, solution. Thus, as the initial liposomes are concentrated during removal of the solution, they flatten and fuse around the flattened edges. During fusion, the material to be encapsulated is believed to be sandwiched between the resulting lamellae of the fused liposomes. When the concentrated admixture is subsequently rehydrated, the lamallae swell and disperse into larger, vesicle structure, that is the resultant liposomes, with a significant fraction of the original material present being encapsulated within the three-dimensional space.

DETAILED DESCRIPTION OF THE PREFERRED EMBODIMENTS

Generally, and as well known, the lipid membranes of liposomes are formed by a bimolecular layer of one or more naturally occurring and/or synthetic lipid compounds having polar heads and nonpolar tails.

Representative, suitable phospholipids or lipid compounds for forming initial liposomes useful in the present invention are phosphatidylcholine ("PC"), both naturally occurring and synthetically prepared, phosphatidic acid ("PA"), phosphatidylserine ("PS"), phosphatidylethanolamine ("PE"), sphingolipids, phosphatidyglycerol ("PG"), spingomyelin, cardiolipin, glycolipids, gangliosides, cerebrosides and the like used either singularly or intermixed such as in soybean phospholipids.

More particularly useful phospholipids include egg phosphatidylcholine ("EPC"), dilauryloylphosphatidylcholine ("DLPC"), dimyristoylphosphatidylcholine ("DOPC"), dipalmitoylphosphatidylcholine ("DPPC"), distearoylphosphatidylcholine ("DSPC"), 1-myristoyl-2-palmitoylphosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dioleoylphosphatidylycholine ("DOPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("PS"), brain sphingomyelin ("BSP"), dipalmitoyl sphingomyelin ("DPSP"), and distearoyl sphingomyelin ("DSSP").

The lipid composition of both the initial liposomes and the resultant liposomes, formed in accordance with the inventive encapsulation method, is normally the same. Where the resultant liposomes are intended for in vivo applications (such as drug delivery), then it is normally desirable that the lipid composition have a transition temperature below body temperature. Liposomes which are composed of phospholipids and which are at temperatures below the characteristic gel-liquid crystalline phase transition temperature are considered "solid," and when above this transition temperature are considered "fluid. " Another consideration in selecting the composition of lipid or lipids for liposome applications is that alkyl-ether linked lipids (rather than ester linked) are more stable to hydrolysis, and hence alkyl-ether linked lipids for the resultant liposomes may be particularly desirable for diagnostic applications.

In addition, other lipids such as steroids, cholesterol, aliphatic amines such as long chain aliphatic amines and carboxylic acids, long chain sulfates and phosphates, dicetyl phosphate, butylated hydroxytoluene, tocophenol, retinol, and isoprenoid compounds may be intermixed with the phospholipid components to confer certain desired and known properties on the initial liposomes and hence the resultant liposomes. Further, synthetic phospholipids containing either altered aliphatic portions, such as hydroxyl groups, branched carbon chains, cycloderivatives, aromatic derivatives, ethers, amides, polyunsaturated derivatives, halogenated derivatives, or altered hydrophilic portions containing carbohydrate, glycol, phosphate, phosphonate, quaternary amine, sulfate, sulfonate, carboxy, amine, sulfhydryl, imidazole groups and combinations of such groups, can be either substituted or intermixed with the phospholipids.

The material to be encapsulated is preferably soluble in the first polar solution, most preferably is substantially water-soluble where the solution is aqueous, but may be substantially insoluble in the selected polar solution so long as the material is of a suitably small size to be dispersed in the polar, or aqueous, solution and subsequently encapsulated within the resultant liposomes. That is, since the diameter of the resultant liposomes (before filtration) will typically range up to about 100 microns, substantially insoluble materials, such as particulate materials, should be sufficiently minute as to be encapsulated within the three-dimensional, confined space of the resultant liposomes. Also, suitable materials for encapsulation will not contain exposed hydrophobic portions which would prevent entrapment, and are less volatile than the polar solution in which the materials are dispersed.

Suitable therapeutic agents for encapsulation include, for example, symphathomimetic agents such as amphetamine sulfate, epinephrine hydrochloride or ephedrine hydrochloride; antispasmodics such as hyosthiamine, atropine, scopolamine hydrobromide, timepidium bromide; bronchodilators such as tretoquinol hydrochloride or isoproterenol hydrochloride; vasodilators such as dilthiazem hydrochloride or dipyridamole, hemostatics such as carbazo-chrome sodium sulfate; vitamins such as bisbutylthiamine; hormones such as insulin; antibiotics such as amino benzylpenicillin, alpha-phenoxypropylpenicillin or alpha-carboxybenzylpenicillin; and antineoplastic agents such as daunorubicin and adriamycin.

Suitable biologically active compounds and diagnostic agents for encapsulation include, for example, RNA, DNA, enzymes, and immunoglobulins, such as IgG and Fab' fragments. Also, various natural and synthetic enzyme substrates for enzyme analyses may be encapsulated.

Suitable reporter molecules for encapsulation include, for example, radioactive ions, chemiluminescent molecules and fluorescent molecules.

The initial liposomes may be formed and dispersed in the polar solution by a variety of known techniques, such as sonication, injection of an alcohol solution of lipid into the aqueous phase, extrusion with a French press under very high pressure, and homogenization, where the majority of initial liposomes therefrom are unilamellar. A particularly preferred technique is by sonication of the lipid composition in distilled water. Preferred lipid concentrations are from about 1 mg/ml to about 50 mg/ml, more preferably from about 5 mg/ml to about 20 mg/ml. The initial liposomes may also be treated so as to be relatively homogeneous in size by means such as sequential extrusion through defined pore size polycarbonate membranes, as described by Olson, et al., *Biochem. Biophys. Acta.* 557: 9–23 (1979).

The material to be encapsulated may be dispersed in the polar solution before, after, or during the formation and dispersal of initial liposomes. It is normally preferable to simply combine the material to be encapsulated with already formed initial liposomes in the selected polar solution at a desired mass ratio. Typical mass ratios of initial liposomes and material are from about 1:1 to about 100:1, more preferably from about 2:1 to about 50:1.

The critical solution removal step to form a concentrated, intimate admixture of the initial liposomes and the material for encapsulation in accordance with the present invention is preferably effected by evaporation of the single phase, polar solvent, either under a reduced pressure (such as about 10–50 mm Hg) or by passing a dry gas over the solution.

For most efficient removal of the aqueous phase, the vessel containing the dispersion can be rotated to spread the dispersion over a larger surface area. Alternatively, the dispersion can be sprayed into an evacuated vessel (flash drying). If the material for encapsulation, or solute, is not sensitive to heat, the solution can be warmed to speed the evaporation process. As the lipid approaches dryness, the originally dispersed vesicles touch and fuse, forming a multilamellar structure that "sandwiches" the solute. Where solution removal is effected by evaporation under a reduced pressure or by means of a dry gas, the concentrated admixture of initial liposomes and material to be encapsulated typically forms a highly viscous, gel-like residue.

Water, or any desired aqueous solution, may then be simply added to redisperse the resultant liposomes, which take the form of a heterogeneous population of unilamellar and multilamellar vesicles containing up to about half of the originally present material. These resultant liposomes may be made more uniform by filtration, centrifugation or gel permeation chromatography. If it is desired to remove solute external to the resultant liposomes, the latter procedure can be used simultaneously.

The following experimental methods, materials and results are described for purposes of illustrating the present invention. However, other aspects, advantages and modifications within the scope of the invention will be apparent to those skilled in the art to which the invention pertains.

EXAMPLE I

A lipid mixture (100 mg lipid) containing 50 mole % phosphatidylserine, 25 mole % phosphatidyl ethanolamine and 25 mole % cholesterol is probe sonicated for 10 min in 10 ml water to form small unilamellar vesicles. Calf thymus DNA (10 mg) in 1 ml water is then added, and the mixture is placed in a rotary evaporator and warmed to 50° C. with nitrogen gas being blown over it during rotation to remove solvent. After removing substantially all the solvent (about one hour), the concentrated, intimate admixture of lipids and DNA is easily hydrated by adding 10 ml of water while rotation is continued, which causes redispersion of the sample. The dispersed sample is withdrawn and passed once through a 1.2 $\mu$m polycarbonate filter, followed by gel filtration to remove soluble DNA external to the vesicles. Upon analysis, the vesicles are found to have encapsulated 47% of the original DNA present, and range in size up to 2 $\mu$m in diameter. The biologically active material so encapsulated is suitable, for example, for delivery of DNA to viable cells.

EXAMPLE II

Egg phosphatidylcholine (100 mg) is dispersed by agitation in 10 ml water containing 1.0 mM 6-carboxylfluorescein ("6-CF"), followed by passage through a French press at 400 kg/cm$^2$ pressure. The solution is taken to substantial dryness as described in Example I, then redispersed by addition of 10 ml water while the flask is rotating. The dispersed liposomes are sized by passage through 1.2 $\mu$m polycarbonate filter, followed by appropriate gel permeation chromatography to remove the external 6-CF. Upon analysis, 22% of the 6-CF is found to encapsulated.

EXAMPLE III

Mixed soybean phospholipid (100 mg) is dissolved in 1.0 ml ethanol and dispersed as small unilamellar vesicles by injection into 10 ml water. Hemoglobin is then added to a final concentration of 1.0 mg/ml, and the solution is dried by rotary evaporation as described in Example I, followed by polycarbonate filtration and gel permeation chromatography to remove external hemoglobin. The resulting vesicles range up to 2 $\mu$m in diameter and were found to encapsulate 36% of the original hemoglobin present.

EXAMPLE IV

Encapsulation of salmon sperm DNA was carried out generally as described by Example II, but with varying amounts of lipid with respect to DNA. Thus, 100 $\mu$g DNA was combined with 0.2 mg/ml, 0.5 mg/ml, 1.0 mg/ml, 2.0 mg/ml, 5.0 mg/ml and 10 mg/ml lipid, respectively. Following rehydration, 1 ml of buffer was added (50 mM Tris-HCl, 5 mM MgCl$_2$, 0.2 mM beta-mercaptoethanol), followed by 20 units pancreatic DNAse to hydrolyze and external DNA that might be binding to vesicle surfaces. After one hour, the liposomes were pelleted (10 kg, 60 min), washed once in buffer, and the DNA content was precipitated by addition of 4 ml ethanol, followed by freezing in liquid nitrogen and centrifugation (30 min, 10,000 X g, $-10°$ C.). The DNA pellet was resuspended in 2 ml potassium phosphate buffer (0.1M, pH 8.0) and scanned spectrophotometrically. The absorbance at 260 nm was then compared with that of the original DNA present and expressed as percent encapsulated. Table I, below, illustrates the encapsulation efficiency as the mass ratio of lipid/DNA is varied between 2:1 to 100:1.

TABLE I

| | Phosphatidylcholine (mg) | | | | | |
|---|---|---|---|---|---|---|
| | 0.2 | 0.5 | 1.0 | 2.0 | 5.0 | 10 |
| Deoxyribonucleic acid (% encapsulated) | 1.1 | 5.0 | 9.8 | 24 | 45 | 39 |

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. A method for encapsulation materials into liposomes comprising:
   providing a single phase, polar solution, the polar solution having initial liposomes dispersed therein and having a quantity of material to be encapsulated dispersed therein, the initial liposomes and the quantity of material being in a mass ratio of from about 2:1 to about 50:1 in the polar solution;

drying the initial liposomes in the presence of the quantity of material by removing substantially all of the polar solution therefrom and forming a highly viscous, concentrated admixture; and, hydrating the concentrated admixture to form resultant liposomes, the resultant liposomes having a portion of the quantity of material previously dispersed in the polar solution of the providing step encapsulated therein, the portion of material encapsulated in the resultant liposomes being at least about 1 wt. % with respect to the quantity of material previously dispersed in the polar solution of the providing step.

2. The method as in claim 1 wherein the polar solution of the providing step is substantially aqueous.

3. The method as in claim 2 wherein the hydrating includes agitating the concentrated admixture in the presence of a second aqueous solution whereby the resultant liposomes are dispersed in the second aqueous solution.

4. The method as in claim 1 wherein the initial liposomes fuse and entrap a portion of the quantity of material during the drying.

5. The method as in claim 1 further comprising:
separating the resultant liposomes from unencapsulated material.

6. The method as in claim 1 or 5 wherein the material encapsulated by the resultant liposomes includes a therapeutic agent, a diagnostic agent, a reporter molecule, or a biologically active compound.

7. The method as in claim 6 wherein the material encapsulated within the resultant liposomes is a biologically active enzyme, protein, immunoglobulin, or nucleic acid.

8. The method as in claim 1 wherein the material encapsulated within the resultant liposomes is a macromolecule.

9. The method as in claim 1 wherein the initial liposomes and the resultant liposomes have at least one lipid bilayer, and a majority of the initial liposomes are unilamellar.

10. The method as in claim 9 wherein the at least one lipid bilayer is formed from one phospholipid or a mixture of phospholipids.

11. The method as in claim 10 wherein the phospholipid is selected from the group consisting of egg yolk phospholipid, soy bean phospholipid, phosphatidyl choline, phosphatidyl ethanolamine, sphingomyelin, phosphatidyl serine, dipalmitoyl lecithin and mixtures thereof.

12. The method as in claim 9 wherein the bilayer comprises a phospholipid or a mixture of phospholipids and at least one other lipid belonging to a class of lipids other than the phospholipids.

13. The method as in claim 12 wherein at least one other lipid is selected from the group consisting of stearylamine, dicetyl phosphate, cholesterol, and tocopherol.

* * * * *